United States Patent
Carter et al.

(10) Patent No.: US 9,026,205 B2
(45) Date of Patent: May 5, 2015

(54) STIMULATING DEVICE

(75) Inventors: Paul Carter, West Pennant Hills (AU); James Patrick, Roseville (AU)

(73) Assignee: Cochlear Limited, Macquarie University, NSW (AU)

( * ) Notice: Subject to any disclaimer, the term of this patent is extended or adjusted under 35 U.S.C. 154(b) by 1171 days.

(21) Appl. No.: 12/440,815

(22) PCT Filed: May 25, 2007

(86) PCT No.: PCT/AU2007/000728
§ 371 (c)(1),
(2), (4) Date: Apr. 29, 2010

(87) PCT Pub. No.: WO2007/137335
PCT Pub. Date: Dec. 6, 2007

(65) Prior Publication Data
US 2010/0256697 A1    Oct. 7, 2010

(30) Foreign Application Priority Data

May 25, 2006    (AU) ................ 2006902833

(51) Int. Cl.
| | |
|---|---|
| A61N 1/00 | (2006.01) |
| A61N 1/36 | (2006.01) |
| A61N 1/05 | (2006.01) |
| A61F 11/00 | (2006.01) |

(52) U.S. Cl.
CPC .......... *A61N 1/36032* (2013.01); *A61N 1/0541* (2013.01); *A61F 11/00* (2013.01)

(58) Field of Classification Search
CPC . A61N 1/0448; A61N 1/0541; A61N 1/0568; A61N 1/0575

USPC .................. 607/3, 46, 55–57, 120
See application file for complete search history.

(56) References Cited

U.S. PATENT DOCUMENTS

| | | | | |
|---|---|---|---|---|
| 4,922,926 | A * | 5/1990 | Hirschberg et al. | 607/120 |
| 6,263,225 | B1 | 7/2001 | Howard, III | |
| 6,309,410 | B1 * | 10/2001 | Kuzma et al. | 607/137 |
| 2004/0078057 | A1 * | 4/2004 | Gibson | 607/3 |
| 2004/0106953 | A1 * | 6/2004 | Yomtov et al. | 607/3 |
| 2004/0127942 | A1 * | 7/2004 | Yomtov et al. | 607/3 |
| 2005/0171579 | A1 * | 8/2005 | Tasche et al. | 607/57 |
| 2006/0287689 | A1 * | 12/2006 | Debruyne et al. | 607/57 |
| 2011/0077579 | A1 * | 3/2011 | Harrison et al. | 604/20 |

FOREIGN PATENT DOCUMENTS

| | | |
|---|---|---|
| WO | 0241666 | 5/2002 |
| WO | 2006083675 | 8/2006 |

OTHER PUBLICATIONS

International Search Report. PCT/AU2007/000728. Mailed Jul. 20, 2007.

* cited by examiner

*Primary Examiner* — Michael Kahelin
*Assistant Examiner* — Mallika D Fairchild (57) ABSTRACT

An implantable apparatus for delivering electrical stimuli to a user, the apparatus including at least a stimulator adapted to generate stimulation signals, an electrode array, said array including a plurality of electrodes for delivering said stimulation signals; and a plurality of release sites for pharmaceutical agents, said release sites being positioned at locations along said array, said release sites being controlled such that said agents can be operatively delivered at selected ones of said locations.

20 Claims, 5 Drawing Sheets

STIMULATING DEVICE

CROSS-REFERENCE TO RELATED APPLICATIONS

The present application is a National Stage application of PCT/AU2007/000728 entitled "A Stimulating Device", filed on May 25, 2007, which claims priority from Australian Provisional Patent Application No. 2006902833, filed on May 25, 2006, which are hereby incorporated by reference.

TECHNICAL FIELD

The present invention relates to systems and devices for delivering pharmaceutical agents in implanted devices, including neural stimulators.

BACKGROUND ART

The use of implanted medical devices to provide electrical stimulation therapy to individuals for various medical conditions has become more widespread in recent times. This has occurred as the advantages and benefits such devices provide become more widely appreciated and accepted throughout the population.

Electrical stimulation can be used for therapeutic effect at various locations within the body. For example, functional electrical stimulation systems may be used to deliver electrical pulses to certain neurons of a recipient to cause a controlled movement of a limb of such a recipient. Also, electrical nerve stimulators are used in applications such as cochlear implants for restoring hearing to people with sensorineural hearing loss.

An implantable hearing prosthesis can provide the benefit of hearing to individuals suffering from severe to profound sensorineural hearing loss. Sensorineural hearing loss is due to the absence or destruction of the hair cells in the cochlea which transduce acoustic signals into nerve impulses. An implantable hearing prosthesis simulates the cochlear hair cells by delivering electrical stimulation to the auditory nerve fibres. This causes the brain to perceive a hearing sensation.

Electrical stimulators pass electric current pulses through nerve tissue causing the nerves to depolarise and fire. The timing and magnitude of the current is usually controllable so that the timing and number of nerves fired is controlled. Each nerve has an energy threshold at which it fires and a time, known as the refractory period, before it can be fired again after stimulation. A problem exists, therefore, when the signals to the electrical stimulator require a nerve to be stimulated repeatedly prior to that nerve being reset to fire again.

It is generally desirable that electrical stimulation systems such as the noted implantable hearing prosthesis consume minimal power. Lower power consumption leads to smaller components and longer battery life.

Pharmaceutical agents can modify the response of nerves to electrical stimulation and induce neural firing in their own right. They are known to be delivered into the area to be treated by a pump mechanism through a tube. The position where the agent is injected is controlled by the placement of the end of the tube and the concentration of agent varies considerably at different parts of the structure.

It is an object of the present invention to provide an improved method and apparatus for the delivery of pharmaceutical agents using implantable devices.

SUMMARY OF THE INVENTION

In a broad form, the invention provides for delivery of a pharmaceutical agent at multiple sites on a device, so that the agent can be delivered selectively at one or more desired locations.

In one aspect, the present invention provides an implantable apparatus for delivering electrical stimuli to a user, the apparatus including at least
  a stimulator adapted to generate stimulation signals;
  an electrode array, said array including a plurality of electrodes for delivering said stimulation signals; and
  a plurality of release sites for pharmaceutical agents, said release sites being positioned at locations along said array, said release sites being controlled such that said agents can be operatively delivered at selected ones of said locations.

Preferably, the amount of agent delivered at each site can be varied and may be varied between the different release sites. Further, there may be a plurality of types of release sites, each type being adapted to deliver a different agent.

Preferably, the implantable array includes a control arrangement, so that delivery of agents is dependant upon a measured neural response. The delivery of the agent may be controlled by a chemical sensor.

Delivery of the agent may be changed on the basis of an operating parameter change selected by the user. Alternatively, the delivery of the agent may be controlled by an injector, wherein the injector includes an electrode which is capable of being heated, wherein on heating of the electrode the agent is heated and expands, the expansion pushing the agent from the release site through a top one-way valve to an outlet port. Advantageously, on cooling of the electrode a bottom one-way valve opens and allows more agent into the release site from an agent reservoir.

Alternatively, the delivery of the agent is controlled by an injector, wherein the injector includes an actuator operable to change the volume of the release site, wherein on operation the agent in the release site is pushed through a top one-way valve to an outlet port. Advantageously, on ceasing operation of the actuator a bottom one-way valve opens and allows more agent into the release site from an agent reservoir.

According to a second aspect of the present invention, there is provided an implantable apparatus for delivering a pharmaceutical agent to a user, the apparatus including at least a plurality of release sites for pharmaceutical agents, said release sites being positioned at locations along the apparatus, said release sites being controlled such that said agents can be operatively delivered at selected ones of said locations.

According to a third aspect of the present invention, there is provided a method of controlling the release of agents from an implantable device, said device including an electrode array and a plurality of release sites, said method including the steps of:
  a) delivering an electrical stimulation at one or more locations;
  b) monitoring the response from the stimulation at each location;
  c) based on the response, determining whether release of a pharmaceutical agent is required, and at what sites;
  d) releasing the agent at selected sites.

According to a fourth aspect of the present invention, there is provided a system for delivering a pharmaceutical agent including
  a stimulator that generates stimulation signals;

at least one electrode member for receiving the stimulation signals and for delivering the stimuli in response to the signals;

a control unit capable of receiving a response from the stimuli;

at least one release site for at least one pharmaceutical agent, said release sites being positioned along the electrode member, the site and timing of the release of the agent being controlled by the control unit in reaction to the response received from the stimuli.

Preferably, the electrode member includes a plurality of electrode arrays.

Preferably, the agent is selected from the list of Brain Derived Neurotrophic Factor (BDNF), sodium ions, or other agents that lower the firing threshold of the nerves.

The system disclosed incorporates electrical stimulation and selected use of pharmaceutical agents to augment the electrical stimulation, whereby the agent is delivered by site-specific targeted delivery rather than delivery from a single site.

By coupling electrical nerve stimulators with the use of pharmaceutical agents in a site specific manner, the agent can be used to selectively fire nerves or to augment the firing of nerves in a site-specific way. This may be used by multi-channel stimulators in which the level and timing of stimulation is varied between different neural sites and in which the concentration of the agent can be varied at different sites, whether associated with the channels or not.

One such use for site-specific application of an agent is, for example, in the situation in which the nerves at a particular site are required to be fired continuously and strongly by electrical stimulation for a period of time, as dictated by the incoming sound and the processing strategy. It may then be advisable to locally deliver an agent that lowers the firing threshold in that region to compensate for any increase in threshold that may occur due to fatigue of the nerve.

Another example is that of stochastic or random firing of the cochlear nerve. An agent such as Brain Derived Neurotropic Factor (BDNF) that lowers the nerve threshold may also be expected to cause the nerve to fire randomly. This is potentially beneficial as this is what happens in the normal hearing ear. Random firing may occur because the nerve threshold is reduced to a point below the random noise associated with the nerve membrane. If the method of administering the BDNF is not site specific, this will result in different and non-controlled concentrations of BDNF at different parts of the cochlear nerve. It may not then be possible to achieve the random firing of nerve fibres at different points along the cochlear nerve as the difference between the maximum and minimum concentrations required to induce spontaneous firing may be smaller than the variations in concentration at the nerve resulting from release of the agent at one site. The present invention in a preferred form allows for release across multiple sites to provide more uniform concentration across the neural structure.

A further example is where an ion pump is used to provide a reservoir of sodium ions that can be injected in a site specific manner along the cochlea. The advantage of using sodium ions over BDNF is that sodium ions are readily available in the body and an ion pump can be used to generate the necessary concentration of sodium ions to be used as the released agent. In principle, then, a system using sodium ions as the pharmaceutical agent could be envisaged that never needed to be maintained or topped up (BDNF and other similar agents need to be replaced when expended).

The present invention, in a preferred form, accordingly allows for the increase in electrical efficiency of the electrical stimulation system by release of agents to reduce the nerve threshold. As a result, the current levels used for stimulation can be decreased and the implant's energy can be used more efficiently.

BRIEF DESCRIPTION OF THE DRAWINGS

An illustrative embodiment of the present invention will be described with reference to the accompanying figures, in which.

DESCRIPTION

The present invention may be implemented in a variety of ways and the embodiments illustrated are to be considered only illustrative constructions.

The embodiment describes the use with an implantable auditory device, in particular a cochlear implant with an external speech processor and implanted receiver/stimulator unit. However, auditory devices include hearing aids, cochlear implants and other prosthetic hearing devices. For example, the present invention may be used in conjunction with any acoustic or electrical auditory device, such as a middle ear implant, intra-cochlear array implant, brain stem implant, implanted mechanical stimulators, implanted acoustic device or any combination of these, or other implanted devices. Further, the stimulation means may be either electrical and acoustic stimulation or a combination of both.

The nature of the stimulation signals will vary with the type of device. For an implanted mechanical stimulation device, this may be raw of modified audio data. For a cochlear implant device, it may be detailed electrode and amplitude data. For an electroacoustic device, it may be both electrical and audio data, or separate signals for each type of device.

Before describing embodiments of the present invention in detail, it is convenient to briefly review the general operation of an intra-cochlear implantable hearing prosthesis system.

An implantable hearing prosthesis system bypasses the hair cells in the cochlea and delivers electrical stimulation to the auditory nerve fibres, thereby allowing the brain to perceive a hearing sensation resembling a natural hearing sensation. A variety of implantable hearing prosthesis systems are described in U.S. Pat. Nos. 4,532,930, 6,537,200, 6,565,503, 6,575,894 and 6,697,674 and US Patent Application No 20050171579, the entire contents and disclosures of which are hereby incorporated by reference herein. An implantable hearing prosthesis system which utilises both electrical stimuli and a facilitation of the production and/or release of naturally occurring agents is described in PCT/AU02/01437, PCT/US06/02793, U.S. patent application Ser. No. 10/494, 995, the entire contents and disclosures of which are hereby incorporated by reference herein. Systems adapted to administer drugs are described in WO 03/072193 and WO 04/050056, the entire contents and disclosures of which are hereby incorporated by reference herein.

Figure 1:
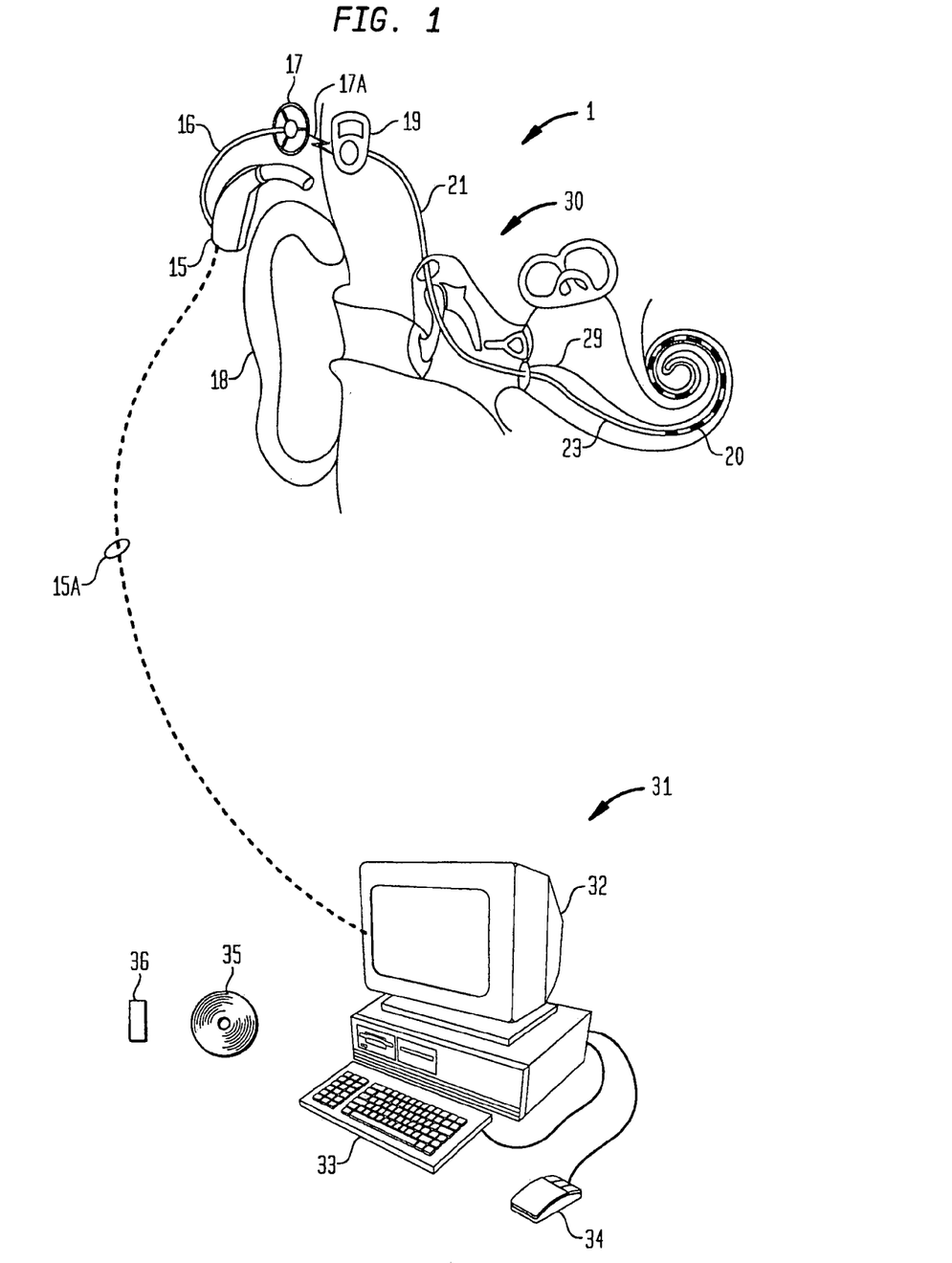
FIG. 1 is a pictorial view of an implantable hearing prosthesis system and a clinician's computer suitable for implementing embodiments of the present invention.

FIG. 1 is a pictorial view of an implantable hearing prosthesis system and a clinician's computer suitable for implementing embodiments of the present invention. In the arrangement illustrated in FIG. 1, an implantable hearing prosthesis system 1 typically comprises an external speech processor unit 15 connected via a lead 16 to an antenna transmitter coil 17. The external speech processor unit 15 includes a microphone, electronics for performing speech processing, and a power source such as a rechargeable or non-rechargeable battery.

In this example, the speech processor unit 15 is configured to fit behind the outer ear 18. Alternatively, the speech processor unit 15 can be worn on the body such as in a pocket, a belt pouch or in a harness. Similarly, the microphone may be provided separately from the speech processor unit 15 and instead mounted on a clothing lapel, for example.

The implantable hearing prosthesis system 1 further includes an implantable receiver/stimulator unit (RSU) 19 connected to an electrode array 23 via a lead 21. The lead 21 includes individual wires extending from each electrode 20 of the array 23 to the receiver/stimulator unit 19 to thus form separate channels.

The RSU 19 is implanted within a recess of the temporal bone and includes a receiver antenna coil for receiving power and data from the transmitter coil 17.

In operation, the electronics within the speech processor unit 15 converts sound detected by the microphone into a coded signal. The external antenna coil 17 transmits the coded signals, together with power, to the receiver/stimulator unit 19 via a radio frequency (RF) link 17A.

The antenna receiver coil 17 receives the coded signal and power for the RSU 19 to process and output a stimulation signal to the electrode array 23.

Once implanted, implant assembly 30 of the IHPS is typically fitted/adjusted to suit the specific needs of the recipient. As the dynamic range for electrical stimulation is relatively narrow and varies across recipients and electrodes, there is a need to individually tailor the characteristics of electrical stimulation for each recipient. Behavioural measurements can be used to establish the useful range for each electrode, and such parameters can be stored within the recipient's speech processor unit 15 for continual use.

These measurements are usually performed on a clinician's computer 31 shortly after surgical implantation of the implant assembly 30. The clinician's computer 31 is a general stand-alone personal computer including a screen 32, keyboard 33 and mouse 34. The computer 31 is loaded with a software program copied from, for example, a medium such as a compact disc (CD) 35 or a memory stick 36 into memory. The software program contains instructions that are carried out by a processor on the clinician's computer 31, to enable the clinician to perform the tests using a suitable interface when connected to the speech processor 15 via communication link 15A.

The finding of a method for reducing firing thresholds of spiral ganglion cells has in turn led to the development of an improved, more efficient, electrical stimulation system that consumes less power, due to a lowering of the firing thresholds of the neurons being stimulated.

Figure 2:
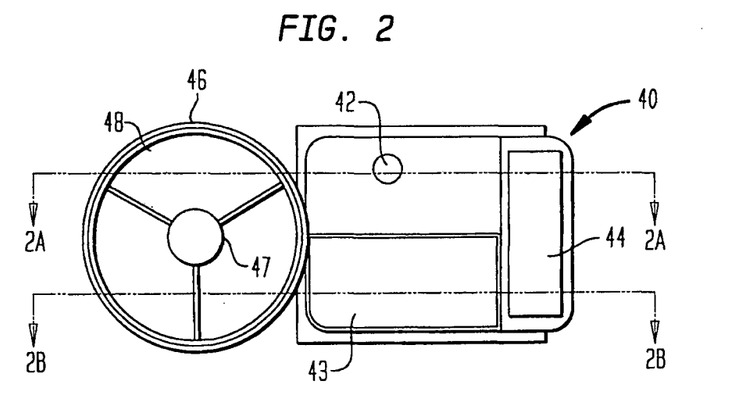
FIGS. 2, 2a and 2b are different views of a totally implantable hearing prosthesis system receiver/stimulator package.
Figure 2A:
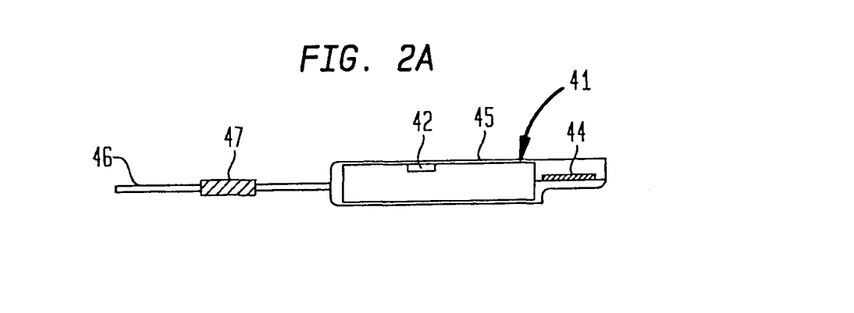
Figure 2B:
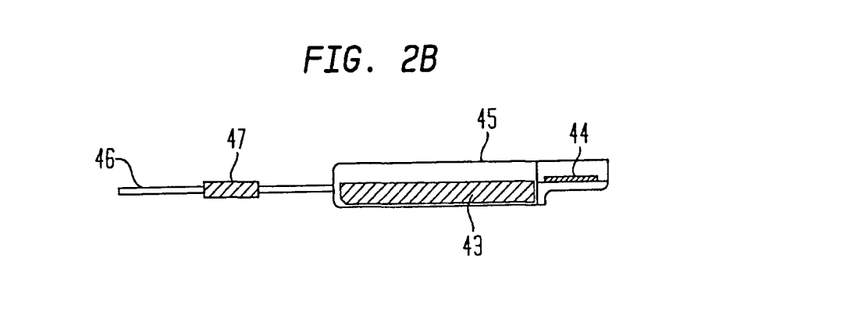

FIGS. 2, 2a and 2b are different views of a totally implantable hearing prosthesis system receiver/stimulator package which is capable of operation, at least for a period of time, without reliance on components worn or carried external to the body of the implantee. An example of the structure and function of a totally implantable prosthetic hearing system is described in U.S. application Ser. No. 10/297,870 and International Application No. PCT/AU01/00769, the entire contents and disclosure of which are hereby incorporated by reference.

Implant 40 is adapted for implantation in a recess formed in the temporal bone adjacent the ear of the implantee that is receiving the implant. Implant 40 may be implanted in a manner similar to how the receiver/stimulator unit 19 shown in FIG. 1 may be implanted.

The implant 40 comprises a biocompatible and hermetically sealed titanium housing 41 that houses the key electronic circuitry 44 of the implant 40. Also housed within the housing 41 are a microphone 42 and a rechargeable battery 43. Prior to implantation, the housing 41 is coated with a layer of silicone or parylene that serves to further protect the implant. Such a coating is well known in the art and will not be further discussed in this application.

In this particular embodiment, the microphone 42 is mounted such that its diaphragm is adjacent one of the surfaces 45 of the housing that faces outwardly following implantation of the housing 41. The depicted microphone 42 is a single cavity microphone but it is envisaged that other microphones, such as a directional dual cavity microphone, could be employed in this system which could perform an equal or similar function.

The electrode array used in conjunction with the implant 40 of the present invention is not shown but can be identical to the array 23 depicted in FIG. 1 or similar. It is, however, preferred that the implant 40 use a Contour array, which may be used in conjunction with corticosteroids to reduce the current required for stimulation.

The rechargeable battery 43 provides power for the microphone 42 and the electronic circuitry 44 housed within the housing 41. Numerous types of batteries could be used with a preferred choice being a Lithium-Ion battery.

The type of battery chosen for this application depends greatly on the system requirements, as would be understood by those skilled in the art.

In the depicted embodiment, the battery 43 is non-removable from the housing 41. It will be appreciated that in other embodiments, the housing 41 could be modified to allow removal of the battery 43 by surgically accessing the housing 41.

The implant 40 is capable of operation whilst the battery 43 is being recharged. In order to isolate the battery 43 from the entire package, a thermal and electrical insulating material is provided between the battery 43 and the surrounding housing 41.

The implant 40 includes an antenna coil 46, which is attached externally of the casing 41. The depicted coil 46 is a 3-turn electrically insulated platinum wire antenna coil. The electrical insulation for the depicted antenna coil 46 is provided by a flexible silicone moulding 48. The antenna coil 46 extends externally from the housing 41 as can be seen in FIG. 2.

The depicted antenna coil 46 is disposed about a centrally located rare earth permanent magnet 47 that is held in the centre of the antenna coil 46 by the silicone moulding 48 surrounding the antenna coil 46. The provision of the magnet 47 assists in the alignment of an external coil unit, such as the external coil 17 depicted in FIG. 1, with the implanted coil 46 via magnetic attractive forces, thereby providing for the system to be used as a conventional cochlear implant system. The magnet 47 is preferably surgically removable so as to allow the implantee to undergo, if required, magnetic resonance imaging (MRI) scanning.

Electrical connection between the coil 46 and the componentry within the housing 41 is provided by two hermetic and insulated ceramic feedthroughs. The coil 46 acts as part of a radio frequency (RF) link to allow bidirectional data transfer between the implant 40 and external devices. The coil 46 also acts a power receiver and so provides a means of inductively charging the battery 43 through the RE link.

The circuitry 44 within the housing 41 is preferably mounted on a flexible circuit board to allow for easier provision of the circuitry 44 within the housing 41. The circuitry 44 includes a speech processor and a stimulation processor incorporated within a single integrated circuit.

In another example, the stimuli is delivered to the Cochlea Nucleus (CN), for example, via an auditory brainstem implant (ABI) or PABI electrode.

Figure 3:
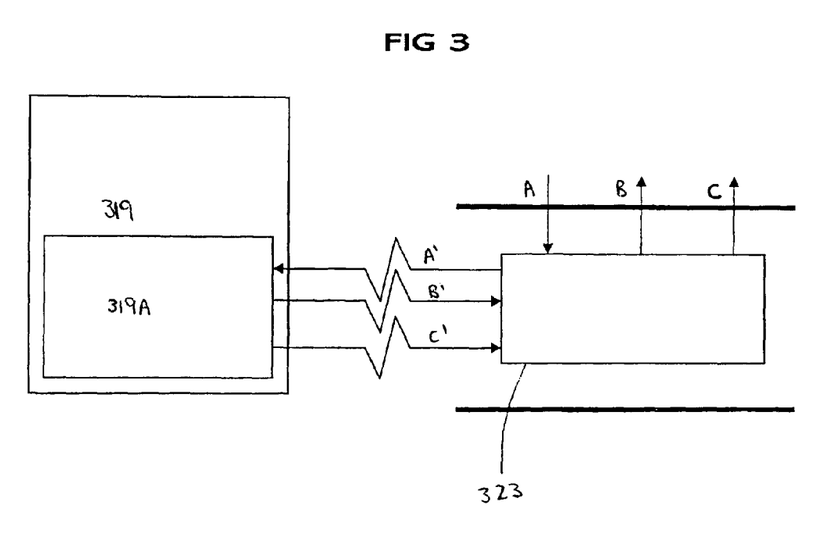
FIG. 3 is a block diagram example of one embodiment of the invention.

A block diagram example of one embodiment of the invention is shown in FIG. 3. The receiver/stimulator part 319 of the cochlear system, shown on the left, receives sound signals and transmits these signals to the internal electrode array 323. The receiver/stimulator part 319 also includes a control block 319A that provides closed loop control of the random firing rate by controlling the level of BDNF administered.

The implanted part of the cochlear system consists of a multi channel cochlear nerve stimulator with an electrode array 323 inserted into the cochlea (the nth site along the cochlea only is shown for clarity). Part of the electrode array 323 includes a mechanism for controlling the administration of pharmaceutical agent, in this case Brain Derived Neurotrophic Factor (BDNF). A response measurement is made, shown by arrow A, and sent to the control block 319A along the path shown by arrow A'. The control block 319A then determines the required delivery of BDNF (arrow B and B') and/or electrical stimulus (arrow C and C') required at the site. The response based feedback mechanism could rely on a chemical sensor to determine the amount of BDNF required to be delivered.

Figure 4:
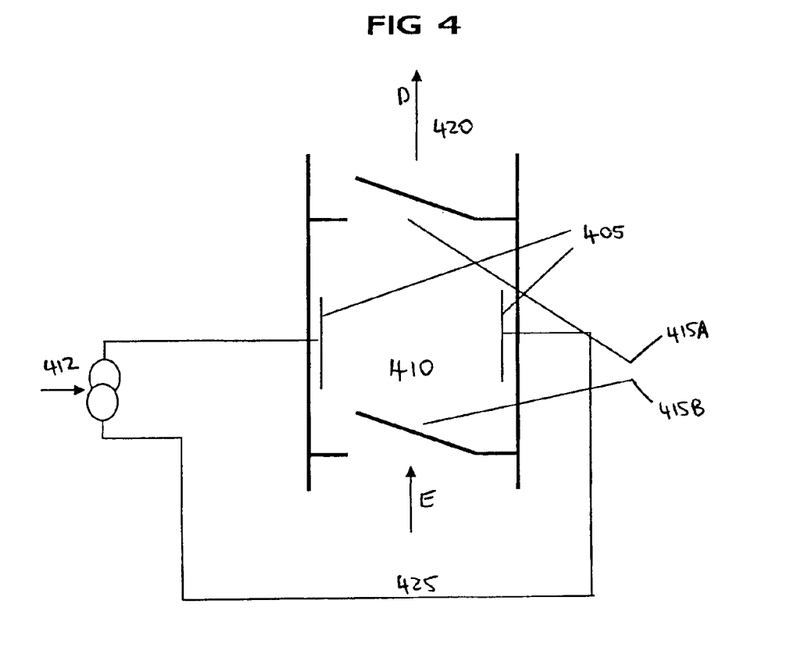
FIG. 4 is a diagram illustrating one method of delivering pulses of BDNF similar to that typically used by ink-jet printers.

One method of delivering pulses of BDNF is similar to that typically used by ink jet printers, as shown in FIG. 4. Pulses or cycles of electrical current are applied to the electrodes 405 in the agent chamber 410 through controlled heating element 412. The agent in chamber 410 is rapidly heated and expands, either through thermal expansion or through cavitation as the agent near the electrodes 405 boils. This expansion pushes some of the agent in the chamber 410 through the top one-way valve 415A and towards the outlet port 420 (as shown by arrow D). The top one-way valve 415A prevents it flowing back towards the chamber 410. When the heating current is stopped the agent cools and contracts. This draws more agent in from the reservoir 425 through the bottom one-way valve 415B in direction E.

For agents that are heat sensitive this method cannot be used because the agents would be damaged. In this case a similar valve system and chamber can be used. However the heating element 412 is replaced with a small electro-mechanical actuator which is configured to change to volume of the (flexible) chamber 410 when activated. Such actuators are commonly used as the driving element in hearing aids. Examples of suitable electromechanical actuators include piezoelectric devices, coil and magnet systems and electret devices. When the actuator is driven with a driving signal the chamber 410 contracts, forcing the agent towards the port 420. When the current is stopped the chamber 410 expands, drawing more agent into the chamber 410.

In both the above systems the amount of agent delivery can be controlled by controlling the amount of driving current applied to the chamber 410 and the rate at which the system is pulsed or cycled.

BDNF is used to lower the threshold of firing of the nerve to the point where a particular background spontaneous nerve firing rate is achieved. The nerve firing rate is measured at locations along the cochlea near the injection sites for the BDNF. Measurement of the background nerve firing rate is achieved using sense electrodes connected to high gain amplifiers in the implant. The control block, located within the body of the cochlear implant, controls the level of background firing of the nerve at a particular site. It does this by measuring the nerve firing rate and then delivering a controlled quantity of BDNF at the same site, the quantity being determined by an appropriate control algorithm running in the control block. The quantity of BDNF being delivered may be determined as part of a feedback system in which a neural response is measured and the amount of BDNF required is calculated and delivered based on the measured neural response.

For different applications the number of sites along the cochlear, N, can be adjusted to suit the level of site specificity required. There may be one site per stimulation electrode or there may be more or less than one. This will depend on how specifically the BDNF can be administered to a particular site (e.g. if the delivery site is very close to the nerve the BDNF can be delivered very accurately to a particular site and the number of sites can be large). It also depends on how locally the firing rate at a given site can be measured (poor localisation means less sites).

Figure 5:
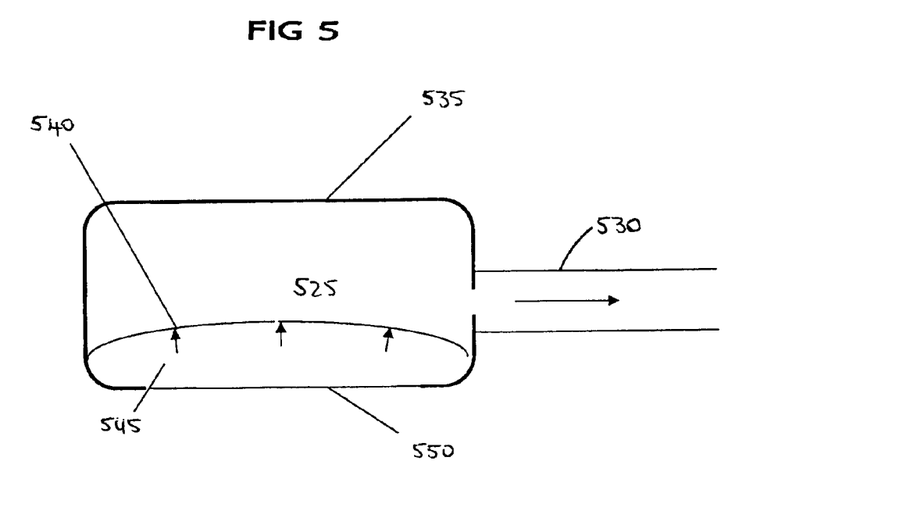
FIG. 5 is a diagram illustrating the delivery of BDNF via osmotic pump.

Delivery of the agent from the reservoir 525 to the injection delivery location is achieved using an osmotic pump as follows. The reservoir 525 is attached to the electrode array by a tube 530 joining the two. The thick external line represents a solid casing 535. The reservoir housing 540 is flexible so that it contracts as the volume of the agent in the reservoir 525 decreases. Fluid 545 with a lower ionic concentration than fluid external to the case 535 is separated from the external fluid by osmotic membrane 550. This is shown schematically in FIG. 5, in a simplified view of an osmotic pump.

Figure 6:
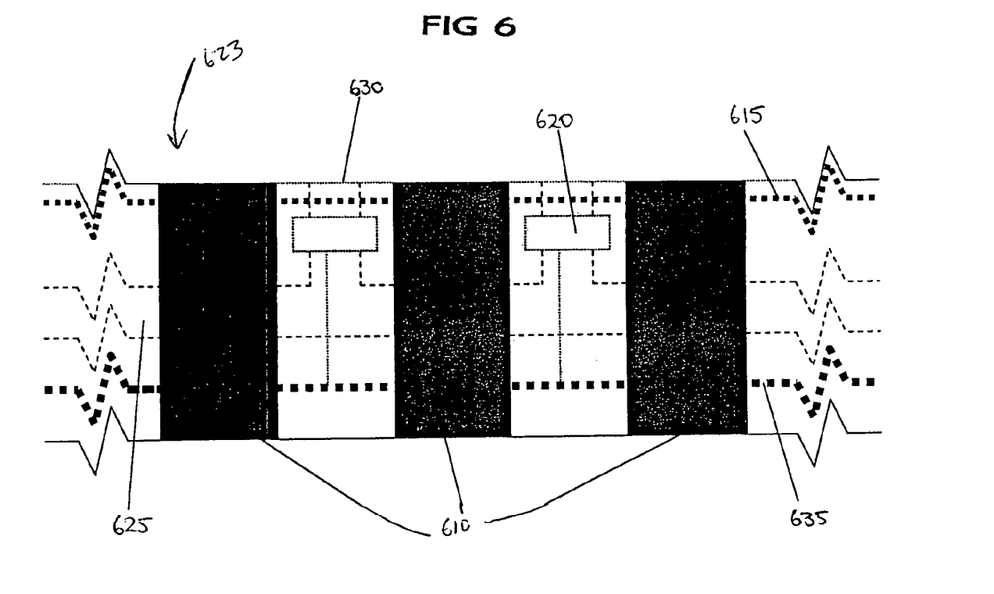
FIG. 6 shows a plan view of an electrode array that may be used in the embodiment.

FIG. 6 shows a plan view of an electrode array 623 that may be used in the embodiment. Items shown with dashed lines are internal to the array 623. The electrode array 623 has the normal electrodes 610 and leads 615. In addition to this the array 623 has a reservoir 625 of pharmaceutical agent, shown at the left of the array 623 shown. This may be positioned in any convenient location. The reservoir 625 is preferably located relatively proximate to the skin of the implant recipient in order that it be topped up easily when the agent is depleted. Top up of the agent may be achieved by a syringe injected through the skin, locating the reservoir 625 and providing the agent to the reservoir 625.

Delivery devices 620 are shown between the electrodes 610, and are associated with a delivery port 630 which facilitates the delivery of the agent to the nerves. The amount and timing of the delivery of the BDNF is controlled through the control port which communicates with the reservoir 625 of agent via the delivery control bus 635. This system is used to dispense controlled amounts of BDNF at sites near the electrodes 610. It will be understood that the number and placement of the delivery ports 630 and delivery devices 620 can be varied and they may not be located between electrodes 610.

The amount of agent released from different delivery devices and ports 620, 630 can be different. Further, the concentration of agent, or the agent itself, can differ between delivery devices and ports 620, 630. The choice of each of these factors may depend on the response measurement A as well as the stimulation strategy being implemented. Therefore, given some systems allow the user to select some operating parameters which affect the stimulation strategy, delivery of the agent can be affected by the user; for example, the user might choose a different strategy when moving from a quiet to a noisy environment to reduce the effect of the surrounding noise. Changes in the agent delivery could also apply when the device itself automatically selects a different stimulation strategy.

Although the present invention has been principally described with reference to a cochlear implant prosthesis, it will be appreciated that this construction can readily be applied to other implant prosthesis in which the site-specific use of a pharmaceutical agent is desirable.

The present invention may be used with any suitable pharmaceutical agent, whether formed in situ or stored. It is not limited in application to the agents described. Similarly, it will be appreciated that different delivery mechanisms and structures may be employed within the broad inventive concept.

The invention claimed is:

1. An implantable apparatus for delivering electrical stimuli to a user, the apparatus including at least
   a stimulator adapted to generate stimulation signals;
   a control unit;
   an elongate member comprising an electrode array configured to be implanted in a cochlea of a recipient and configured to adopt a curved configuration inside the cochlea, said elongate member including,
   a plurality of electrodes for delivering said stimulation signals; and
   a plurality of release sites for at least one pharmaceutical agent, said release sites being positioned at locations along said array, each of said release sites including an outlet port, an agent chamber, and a top one-way valve located between the outlet port and the agent chamber, the top one-way valve allowing the at least one agent to be pushed from the agent chamber to the outlet port and thereafter preventing the at least one agent from flowing back into the agent chamber, said release sites being controlled by the control unit such that said at least one agent can be operatively delivered at selected ones of said locations.

2. The apparatus of claim 1, wherein the amount of agent delivered at each site can be varied by the control unit.

3. The apparatus of claim 1, wherein the concentration of the at least one agent is varied between the different release sites by the control unit.

4. The apparatus of claim 1, wherein said array includes a plurality of types of release sites, each type being adapted to deliver a different agent.

5. The apparatus of claim 1, wherein the implantable apparatus includes a device configured to measure a neural response, and wherein the control unit is configured such that the delivery of said at least one agent is dependent upon a measured neural response.

6. The apparatus of claim 1, wherein the implantable apparatus includes a chemical sensor, and wherein the implantable apparatus is configured such that delivery of the at least one agent is based on information obtained by the chemical sensor.

7. The apparatus of claim 1, wherein the implantable apparatus is configured such that delivery of the at least one agent is changed on the basis of an operating parameter change selected by the user.

8. The apparatus of claim 1, wherein:
   the release sites include an injector; and
   the delivery of the agent is performed by the injector, wherein the injector includes a heating electrode, wherein on heating of the heating electrode the at least one agent is heated and expands, the expansion pushing the at least one agent from the agent chamber through the top one-way valve to the outlet port.

9. The apparatus of claim 8, wherein:
   the release sites further include a bottom one-way valve and an agent reservoir connected thereto; and
   on cooling of the electrode, the bottom one-way valve opens and allows more agent into the agent chamber from the agent reservoir.

10. The apparatus of claim 1, wherein:
    the release sites include an injector; and
    the delivery of the agent is performed by the injector, wherein the injector includes an actuator operable to change the volume of the agent chamber, wherein the implantable apparatus is configured such that on operation the at least one agent in the agent chamber is pushed through the top one-way valve to the outlet port.

11. The apparatus of claim 10, wherein:
    the release sites further include a bottom one-way valve and an agent reservoir connected thereto; and
    on ceasing operation of the actuator, the bottom one-way valve opens and allows more agent into the agent chamber from the agent reservoir.

12. The array according to claim 1, wherein the agent is selected from the list of Brain Derived Neurotrophic Factor, sodium ions, or other agents that lower the firing threshold of the nerves.

13. The apparatus of claim 1, wherein each of said release sites includes a bottom one-way valve, the agent chamber located between the top one-way valve and the bottom one-way valve, the bottom one-way valve allowing more agent to be drawn into the agent chamber.

14. An implantable apparatus for delivering a pharmaceutical agent to a user, the apparatus comprising:
    a control unit;
    an elongate member comprising an electrode array configured to be implanted in a cochlea of a recipient and configured to adopt a curved configuration inside the cochlea, the elongate member including:
    a plurality of stimulation electrodes configured to deliver stimulation signals; and
    a plurality of release sites for at least one pharmaceutical agent, said release sites being positioned at locations along the array, each of said release sites including an outlet port, an agent chamber, and a top one-way valve located between the outlet port and the agent chamber, the top one-way valve allowing the at least one agent to be pushed from the agent chamber to the outlet port and thereafter preventing the at least one agent from flowing back into the agent chamber, said release sites being controlled by the control unit such that said at least one agent can be operatively delivered at selected ones of said release sites.

15. The apparatus of claim 14, wherein each of said release sites includes a bottom one-way valve, the agent chamber located between the top one-way valve and the bottom one-way valve, the bottom one-way valve allowing more agent to be drawn into the agent chamber.

16. A method of controlling the release of at least one agent from an implantable device, said device including an electrode array and a plurality of release sites, said method including the steps of:
    delivering an electrical stimulation at one or more locations;
    monitoring the response from the stimulation at each location;

based on the response, determining whether release of a pharmaceutical agent is required, and at what sites; and releasing the at least one agent at selected sites, through top one-way valves, from agent chambers located on opposite sides of the top one-way valves, wherein the electrode array is an elongate array configured to be implanted in a cochlea of a recipient and configured to adopt a curved configuration inside the cochlea.

17. The method of claim 16, wherein:

the at least one agent includes pharmaceutical agents;

the electrode array is an elongate array configured for a cochlear implant, the array having a plurality of release sites for the pharmaceutical agents; and the step of delivering an electrical stimulation at one or more locations includes delivering an electrical stimulation at one or more locations along said array.

18. The method of claim 16, which includes drawing more agent into the agent chambers through bottom one-way valves, wherein each agent chamber is located between one of the top one-way valves and one of the bottom one-way valves.

19. A system for delivering a pharmaceutical agent, the system including:

a stimulator that generates stimulation signals;

at least one electrode member, configured to be implanted in a cochlea of a recipient and configured to adopt a curved configuration inside the cochlea, for receiving the stimulation signals and for delivering the stimuli in response to the signals;

a control unit configured for receiving a response from the stimuli; and a plurality of release sites for at least one pharmaceutical agent, said release sites being positioned along the electrode member, each of said release sites including an outlet port, an agent chamber, and a top one-way valve located between the outlet port and the agent chamber, the top one-way valve allowing the at least one agent to be pushed from the agent chamber to the outlet port and thereafter preventing the at least one agent from flowing back into the agent chamber, the site and timing of the release of the at least one agent being controlled by the control unit in reaction to the response received from the stimuli.

20. The system of claim 19, wherein each of said release sites includes a bottom one-way valve, the agent chamber located between the top one-way valve and the bottom one-way valve, the bottom one-way valve allowing more agent to be drawn into the agent chamber.

* * * * *